(12) United States Patent
Ströfer et al.

(10) Patent No.: US 7,230,130 B2
(45) Date of Patent: Jun. 12, 2007

(54) PROCESS FOR PREPARING METHYLENEDIANILINE AND METHYLENEBIS (PHENYLISOCYANATE)

(75) Inventors: Eckhard Ströfer, Mannheim (DE); Jan Jacobs, Hoogerheide (NL); Wilfried Seyfert, Kapellen (BE); Hans Volkmar Schwarz, Waterloo (BE); Olaf Schweers, Ludwigshafen (DE); Volker Scharr, Senftenberg (DE); Ulrich Penzel, Tettau (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 236 days.

(21) Appl. No.: 10/843,046

(22) Filed: May 11, 2004

(65) Prior Publication Data

US 2005/0014975 A1    Jan. 20, 2005

Related U.S. Application Data

(63) Continuation of application No. 10/152,489, filed on May 21, 2002, now Pat. No. 6,831,192, which is a continuation of application No. 09/601,097, filed on Sep. 8, 2000, now Pat. No. 6,433,219.

(51) Int. Cl.
*C07C 263/10* (2006.01)
(52) U.S. Cl. .................. 560/347; 560/358; 560/359
(58) Field of Classification Search ............... 560/347, 560/358, 359
See application file for complete search history.

(56) References Cited

U.S. PATENT DOCUMENTS 3,471,543 A    10/1969   Sayigh
4,189,354 A    2/1980    Ellendt et al.
5,053,539 A    10/1991   Yano et al.
5,286,760 A *  2/1994    Bolton et al. ............... 521/160
6,433,219 B1 * 8/2002    Strofer et al. ............... 560/347

FOREIGN PATENT DOCUMENTS

| CA | 2180285 | 12/1996 |
| DE | 2134756 | 7/1971 |
| DE | A 238042 | 8/1986 |
| DE | 295 628 A5 | 11/1991 |
| EP | 0 451 442 A2 | 10/1991 |
| EP | A451422 | 10/1991 |
| EP | A 751 118 | 1/1997 |
| GB | 1298258 | 11/1972 |
| GB | 1 378 423 | 12/1974 |
| GB | 1450632 | 9/1976 |

* cited by examiner

Primary Examiner—Taylor Victor Oh
(74) Attorney, Agent, or Firm—Fernando A. Borrego

(57) ABSTRACT

A process for preparing methylenedianiline by reacting aniline with formaldehyde in the presence of acid catalysts comprising, in a semicontinuous process, introducing aniline with or without acid catalyst, feeding formaldehyde with or without acid catalyst through a mixing element into a circuit in which aniline with or without acid catalyst and with or without previously added formaldehyde is circulated and, after feeding in at least 50% of the total amount of formaldehyde to be fed in, heating the reaction mixture to a temperature above 75° C.

Figure 1:
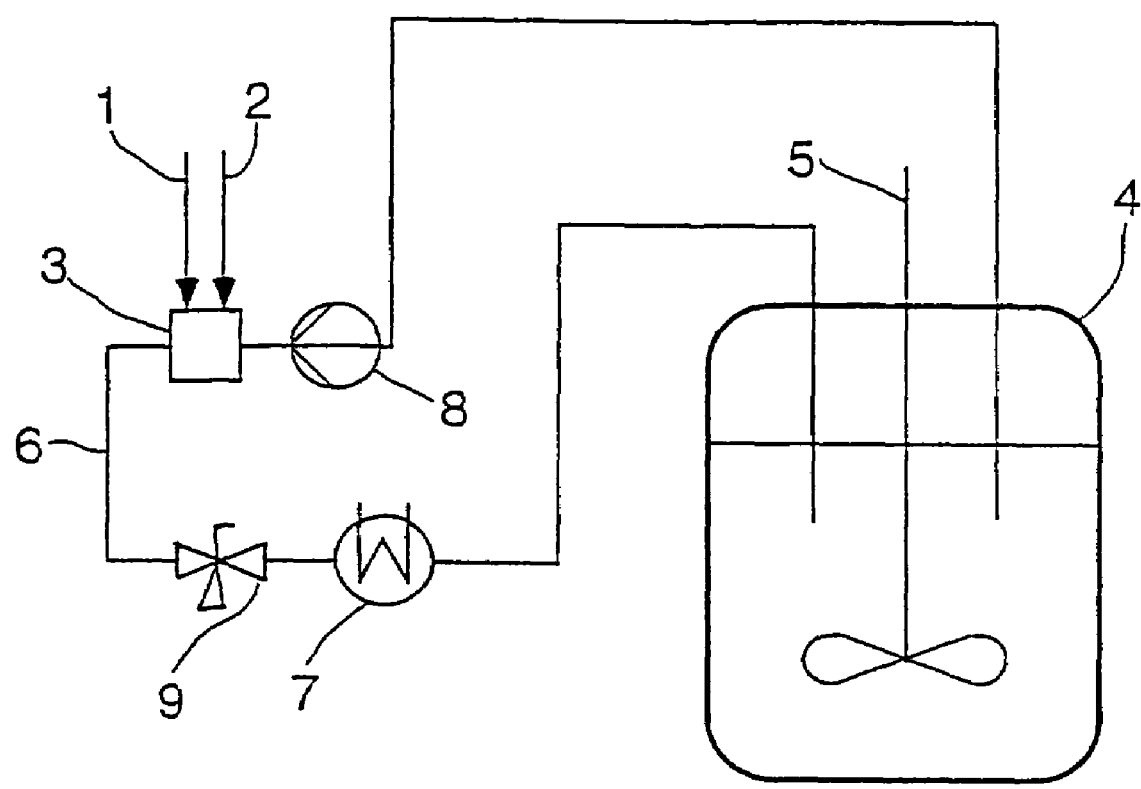

In addition, the invention relates to a process for preparing polyisocyanates by phosgenation of amines obtainable in this manner and to the polyisocyanates obtainable by this process.

2 Claims, 2 Drawing Sheets

PROCESS FOR PREPARING METHYLENEDIANILINE AND METHYLENEBIS (PHENYLISOCYANATE)

This application is a continuation of U.S. application Ser. No. 10/152,489, filed May 21, 2002 now U.S. Pat. No. 6,831,192, which is a continuation of U.S. application Ser. No. 09/601,097, filed Sep. 8, 2000, now U.S. Pat. No. 6,433,219.

The present invention relates to a process for preparing methylenedianiline by reacting aniline with formaldehyde in the presence of acid catalysts, the mixtures which can be prepared by this process comprising methylenedianiline, a process for preparing polyisocyanates by phosgenation of these mixtures comprising methylenedianiline, and polyisocyanates obtainable in this manner.

The preparation of methylenedianiline (also termed MDA below), is generally known and is customarily carried out by continuous or batchwise reaction of aniline with formaldehyde in the presence of acid catalysts. In this reaction, whose main product is 4,4'-MDA, the unwanted byproduct N-methyl-MDA is formed to a small extent. This byproduct is disadvantageous, in particular in the subsequent reaction of the MDA with phosgene to prepare methylenebis(phenyl isocyanate), also termed MDI, since the N-methyl-MDA is the precursor compound for chlorinated byproducts in the MDI and chlorine contents in the MDI as low as possible are sought.

To decrease N-methyl-MDA as byproduct in the preparation of MDA, various processes are known.

Thus, U.S. Pat. No. 5,286,760, for continuous MDA preparation, describes partial neutralization of the reaction mixture between the stage of condensation of two molecules of aniline and one molecule of formaldehyde and the subsequent rearrangement of the intermediate aminobenzylamines, abbreviated as ABA, to give MDA.

EP-A 451 442 and DD-A 238 042 disclose, for a continuous process, the addition of formaldehyde over a plurality of process stages.

Processes for decreasing the byproduct are also known for batchwise processes. DD-A 295 628 describes the addition of formaldehyde in two steps during the condensation stage, in the first addition the main amount of formaldehyde being added at a low temperature and the second addition of the remaining formaldehyde being performed at the same or higher temperature.

A disadvantage in these processes is the insufficient decrease of the N-methyl-MDA content in the product mixture, so that there is still a need for improvement.

Processes for preparing MDI from MDA by phosgenation are generally known.

It is an object of the present invention to develop a process for preparing methylenedianiline by reacting aniline with formaldehyde in the presence of acid catalysts which minimizes the N-methyl-MDA content as an unwanted byproduct. Such an MDA should be used, in particular, in an improved process for preparing methylenebis(phenyl isocyanate) (MDI), which should make accessible an MDI having improved properties, in particular a low chlorine content and a light color.

We have found that this object is achieved according to the invention, in a semicontinuous process, by introducing aniline with or without acid catalyst, feeding formaldehyde with or without acid catalyst through a mixing element into a circuit in which aniline with or without acid catalyst and with or without previously added formaldehyde is circulated and, after feeding in at least 50% of the total amount of formaldehyde to be fed in, heating the reaction mixture to a temperature above 75° C.

This novel procedure permits a higher content of higher MDA oligomers to be obtained than is possible by a continuous procedure at high molar ratios of aniline to formaldehyde without recycling the MDA. Thus, by the process according to the invention, minimizing the content of unwanted byproducts is possible.

The reaction according to the invention of aniline with formaldehyde, preferably in the presence of acid catalysts, is performed according to the invention semicontinuously, i.e. one reaction component, the aniline and preferably the acid catalyst, is introduced and the second reaction component, the formaldehyde with or without acid catalyst, is added to the first reaction component. Preferably, the process according to the invention is carried out in such a manner that aniline and acid catalyst are introduced and formaldehyde is added to this first reaction component. The reaction is customarily carried out at temperatures of from 20 to 150° C. Preferably, the process according to the invention is carried out in such a manner that the formaldehyde is added to the reaction mixture in the circuit, i.e. to the aniline, the acid catalyst and to formaldehyde which has possibly been previously added and reaction products, up to an amount of at least 50% of the total amount of formaldehyde to be fed, preferably up to complete addition of all of the formaldehyde, at a reaction mixture temperature in the circuit of from 20 to 75° C., preferably from 20 to 50° C.

The temperature effects the isomeric distribution of the methylenedianiline in the product. If, preferentially, 2,2'- and/or 2,4'-methylenedianiline are to be prepared, a high temperature may be advantageous. The reaction mixture can be heated by generally customary devices, e.g. by heat exchangers in the pumped circuit or a second pumped circuit and/or via the reactor wall.

The reaction mixture, after feeding into it at least 50% of the total amount of formaldehyde to be fed, is, preferably towards the end of the feed of formaldehyde solution, particularly preferably after the complete addition of the entire amount of formaldehyde to the reaction mixture, heated, preferably for a period of at least 0.2 hours, particularly preferably from 0.2 to 48 hours, in particular from 0.2 to 6 hours, at a temperature of above 75° C., preferably above 90° C., particularly preferably from 110 to 150° C. This heating offers the advantage that the handleability of the reaction mixture is simplified, since the reaction mixture has a lower viscosity at the higher temperature. At the same time, during this heating, unwanted byproducts in the reaction mixture are broken down or rearranged in an ageing phase. The reaction mixture can be aged under these preferred conditions in the apparatus in which the reaction of formaldehyde with aniline was carried out, or else batchwise or continuously in another apparatus into which the reaction mixture can be transferred after complete addition of the formaldehyde. For example, the reaction mixture can be aged in the apparatus in which the formaldehyde solution is fed or was fed. It is also possible to pass the reaction mixture from the apparatus into at least one further reactor, for example a tubular reactor and/or stirred tank, and to perform the ageing in this reactor (these reactors) at a temperature of above 75° C. Preferably, the reaction mixture, after complete addition of the formaldehyde, is transferred to another apparatus in which the ageing is completed.

The reaction mixture can thus be passed into, for example, tubular reactors, stirred tanks, stirred tank cascades, combinations of stirred tanks and tubular reactors in which the reaction to give MDA can be completed.

The reaction mixture comprising MDA can be worked up after the reaction by generally known processes, for example by neutralization, phase separation, distillation and/or chromatographic separation methods, preferably by neutralization and removal of water, aniline and possibly other unwanted minor components by distilling these substances.

The starting components formaldehyde, aniline and acid catalyst can be used at customary purities, the formaldehyde being able to be in equilibrium with higher molecular weight addition products such as poly(oxymethylene)glycols. The formaldehyde can be used in customary, for example aqueous, solutions having a formaldehyde content of from 10 to 60% by weight, based on the weight of the solution.

The reaction mixture can be circulated in a suitable apparatus by generally customary devices, for example pumps. The rate at which the reaction mixture is circulated is preferably from 1 to 6 m/sec. The formaldehyde solution can be fed via a reaction mixing pump, such as described in DE-A 4220239 or via a nozzle system, e.g. a ring-gap nozzle, built into the pump circuit. In the case of the reaction mixing pump, the device not only serves for feeding in the formaldehyde and preferably complete mixing, but also for moving the reaction mixture in the apparatus. If a nozzle is used, the reaction mixture can be moved in the apparatus by conventional pumps known in chemistry. The mixing energy dissipated during the feed of formaldehyde into the reaction mixture in the mixing zone of the mixing element, i.e. for example the nozzle or the reaction mixing pump, is preferably from 100 to 100,000 W/l. The quantity in the pumped circuit is in a ratio to the quantity of formaldehyde solution fed into the circuit of preferably at least 20:1.

As acid catalyst, use can be made of catalysts generally known for this reaction, for example mineral acids such as phosphoric acid, sulfuric acid and/or hydrochloric acid (HCl); preferably HCl is used.

The molar ratio of aniline to acid catalyst in the reaction mixture is customarily from 1:0.6 to 1:0.01, preferably from 1:0.3 to 1:0.05. This molar ratio applies in particular to the particularly preferred embodiment in which aniline and acid catalyst are introduced and then formaldehyde and no further acid catalyst is added.

The molar ratio of aniline to the total amount of formaldehyde to be added is customarily from 1.7:1 to 7.2:1, preferably from 1.9:1 to 5.1:1. The formaldehyde is preferably fed into the circuit through a nozzle or a reaction mixing pump. In order to avoid unwanted parallel reactions leading to byproducts, the formaldehyde is preferably added in such a manner that as rapid and complete mixing as possible takes place with the reaction mixture which is situated in the apparatus. This can be achieved, for example, by generating a turbulent flow in the mixing chamber.

In the process according to the invention, preferably in one apparatus, aniline and preferably HCl as acid catalyst are introduced, mixed, circulated, for example by a connected conventional pump, and formaldehyde is added to this reaction mixture, preferably via a reaction mixing pump or nozzle. The formaldehyde can be added in such a manner that constant volumes per unit time are fed into the reaction mixture until there is a suitable molar ratio of aniline to formaldehyde in the reaction mixture. Preferably, the addition is performed in such a manner that, per minute, from 0.05 to 2% of the original volume of the aniline in the apparatus are passed as volume of formaldehyde solution into the reaction mixture. Instead of introducing a constant volume of formaldehyde per unit time, the formaldehyde can be added to the reaction mixture in such a manner that the volume of the formaldehyde added per unit time decreases in accordance with a mathematical function as the addition progresses. Preference is given to an addition rate which is constant, falling linearly, or falling in stages. Furthermore, the formaldehyde can be introduced in pulses into the reaction mixture, in which case a regular or irregular pulse frequency and addition rate can be selected. The total amount of formaldehyde to be introduced should preferably correspond to the molar ratios described at the outset in relation to the amount of aniline. In this batchwise procedure, the reaction mixture is emptied from the apparatus after the desired conversion rate and further worked up if necessary.

The reaction according to the invention can be carried out, for example, in an apparatus which has 1: feed lines for aniline and acid catalyst,
2: feed line for formaldehyde,
3: at least one mixing element, for example a reaction mixing pump or nozzle through which the formaldehyde is fed into the apparatus,
4: at least one reactor having
5: optional devices for mixing the reaction mixture,
6: a pipe system which, starting from the reactor, makes circulation of the reaction mixture possible,
7: a device for heating the reaction mixture and
8: an optional pump which circulates the reaction mixture in (6) and
9: at least one connection for taking off the reaction mixture.

An apparatus of this type is shown in FIG. 1 by way of example, in which figure it may be noted that aniline and acid catalyst can be added either together, as shown in FIG. 1, or separately, at substantially any point of the apparatus, for example by addition to the reactor (4) or through connections to the reaction mixing pump or nozzle (3). The devices, 7, 8 and, in particular, 9, can also be disposed substantially anywhere, for example, in the case of the connection 9, on the reactor 4 as well.

The selected capacity of the reactor (4) can vary depending on the desired conversion rate. The selected diameter, which can also vary, and the length of the pipe system (6) can also vary substantially as desired depending on batch size. For components (1) to (9) conventional devices can be used, as already described for components (3) and (7). An apparatus suitable for carrying out the process according to the invention can consist of materials customary for this purpose, for example steel/enamel or stainless steel alloys.

The process product, i.e. the mixture comprising methylene-dianiline, for example 2,2'-, 2,4'-, and/or 4,4'-MDA, preferably comprises less than 0.09% by weight of N-methyl-MDA and is preferably used for the known synthesis of methylenebis(phenyl isocyanate), known as MDI, for example 2,2'-, 2,4'- and/or 4,4'-MDI and polymeric MDI, for example by conventional phosgenation of polyamines. The phosgenation can be carried out in customary, particularly preferably inert, solvents, e.g. toluene, monochlorobenzene and/or dichlorobenzene, in conventional reactors, for example stirred tanks, stirred tank cascades, columns and/or tubular reactors at known temperatures of, for example, from 50 to 150° C., preferably from 70 to 120° C., particularly preferably from 70 to 100° C. and at a pressure of from 0.5 to 10 bar, particularly from 0.8 to 5 bar, particularly preferably from 0.8 to 1.5 bar. The crude MDI prepared by phosgenation can be purified by customary processes, for example distillation. Preferably, in a first purification operation, phosgene with or without solvent can be removed, preferably substantially, particularly preferably completely, from the phosgenation reaction mixture, i.e. from the crude MDI. This purification step can preferably be carried out by a stripping process. In a stripping process of this type, the crude MDI can be passed into one or more apparatuses having a large internal surface area and can be distributed onto its surface, so that readily volatile components can escape. The apparatus can be, for example and preferably, a falling-film or thin-film evaporator or a packed column of suitable design. Inert gases can be fed in as stripping medium and/or vacuum can be applied over the apparatus. The temperatures during this stripping process are preferably below 200° C., particularly preferably from 50 to 190° C. Preferably, the desired monomeric MDI, for example 2,2'-, 2,4'- and/or 4,4'-MDI and/or mixtures comprising at least two of these isomers, are separated off by a suitable process, preferably by distillation, for example at pressures of from 2 to 50 mbar, preferably from 2 to 20 mbar, and temperatures of from 150 to 250° C., preferably from 180 to 230° C., and/or preferably by crystallization, for example by fractional crystallization.

Particularly preferably, the crude MDI is purified by removing phosgene, HCl with or without solvent, for example in a previously described stripping process, possibly under vacuum or with feed of inert gas, from the crude MDI at a temperature of <150° C., preferably from 50 to 149° C., after preferably complete removal of the phosgene, separating off solvent with or without chlorine-containing compounds from the isocyanate at a temperature of □190° C., preferably from 150 to 190° C., for example in a previously described stripping process, the purification steps being able to be carried out by the previously described apparatuses, and subsequently separating off the desired monomeric MDI, for example 2,2'-, 2,4'- and/or 4,4'-MDI and/or mixtures comprising at least two of these isomers, by a suitable process, preferably by distillation, for example at pressures of from 2 to 50 mbar, preferably from 2 to 20 mbar, and temperatures of from 150 to 250° C., preferably from 180 to 230° C., and/or preferably by crystallization, for example fractional crystallization.

These purification processes offer the advantage that chlorine-containing compounds which lead to adverse properties in the desired isocyanate are removed from the isocyanate and at the same time the formation of coloring components is suppressed.

The process according to the invention for preparing methylenebis(phenyl isocyanate) can thus be carried out, in a semicontinuous process, by introducing aniline and acid catalyst, the molar ratio of aniline to acid catalyst being from 1:0.6 to 1:0.01, feeding formaldehyde through a nozzle or a reaction mixing pump into a circuit in which aniline and acid catalyst with or without previously added formaldehyde can be circulated at a temperature of from 20 to 75° C., after feeding in at least 50% of the total amount of formaldehyde to be fed in, heating the reaction mixture for a period of at least 0.2 hours at a temperature above 75° C., the molar ratio of the aniline introduced to the total amount of formaldehyde to be added being from 1.7:1 to 7.2:1, neutralizing the resulting methylenedianiline, separating off water and aniline by distillation, phosgenating the purified methylenedianiline at a temperature of from 50 to 150° C. and a pressure of from 0.5 to 10 bar in the presence or absence of inert solvents, removing phosgene, HCl and possibly solvent, for example in a previously described stripping process, from the crude MDI at a temperature below 150° C. possibly under vacuum or feeding in inert gas, then separating off solvent with or without chlorine-containing compounds, for example in a previously described stripping process, from the isocyanate at a temperature of □190° C. and then separating off the desired monomeric MDI, for example 2,2'-, 2,4'- and/or 4,4'-MDI and/or mixtures comprising at least two of these isomers, by a suitable process, preferably by distillation, for example at pressures of from 2 to 50 mbar, preferably from 2 to 20 mbar, and temperatures of from 150 to 250° C., preferably from 180 to 230° C., and/or preferably by crystallization, for example fractional crystallization.

The polyisocyanates prepared using the methylenedianiline according to the invention have the advantage, in particular, that they possess a low hydrolyzable chlorine content. In addition, the isocyanate prepared according to the invention has a color which is desirably very light. These advantages are not only due to the preparation according to the invention of the methylenedianiline having the low byproduct content, but are also due to the fact that the phosgenation of the amines and the product workup are carried out at low pressures and thus low temperatures. This defined combination of many process parameters beginning with aniline to the final bis(isocyanate) leads to the particularly advantageous products according to the invention.

Preferably, the isocyanates attainable according to the invention have a hydrolyzable chlorine content of <0.1% and an iodine color index of <30 at a dilution of 1:5 in monochlorobenzene.

The examples illustrate the invention.

COMPARATIVE EXAMPLE 1

The reaction was carried out in an apparatus which consisted of a stirred-tank cascade having three reactors which had capacities of 700, 800 and 800 ml, and a packed tube. The reaction temperatures in the reactors were set at 40 (first stirred tank), 70 (second stirred tank), 80 (third stirred tank) and 120° C. (tubular reactor) by external cooling and/or heating. The packed tube had a total volume of 5000 ml and an internal tube diameter of 30 mm. The agitator speed in the reactors of the stirred-tank cascade was in each case 500 rpm. 1264 µl of aniline, which had previously been mixed with 422 g/h of 30% strength aqueous hydrochloric acid, were added to the first reactor. At the first reactor was situated an external pumped circuit having a static or dynamic mixer into which 341 g/h of a 50% strength formaldehyde solution in water were added by a pump. The product mixture from the tubular reactor was neutralized using sodium hydroxide solution. Phase separation was then performed at a temperature of from 70 to 80° C. The organic phase was separated off and washed with 1.5 times the volume of warm water. Excess aniline was distilled off from this purified phase under reduced pressure and recirculated to the first reactor. 24 h after starting up the plant, the reaction mixture was in a steady state and samples of the organic phase were taken. The N-methyl-MDA content in the resulting product was 0.26% by weight. This polyamine was reacted in two stages with phosgene in a conventional process for preparing isocyanates. The hydrolyzable chlorine content in this polyisocyanate was 0.22%.

EXAMPLE 1

Figure 2:
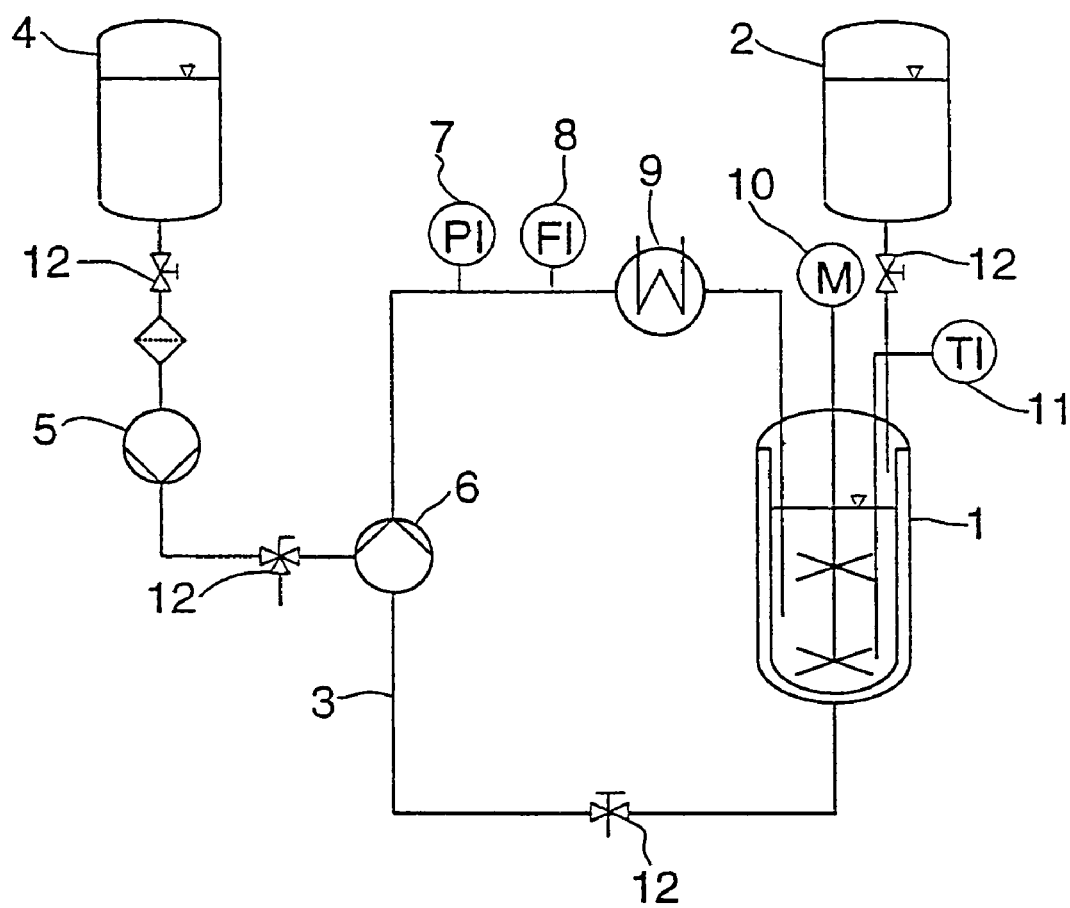

An apparatus as shown in FIG. 2 was employed. In this FIG. 2, the reference numbers designate the following:

1: reactor
2: reservoir tank, feed of aniline and HCl
3: reaction mixture circulation circuit 4: reservoir tank, feed of formaldehyde solution
5: metering pump
6: mixing element, formaldehyde solution admission
7: pressure gage
8: flowmeter
9: heat exchanger
10: agitator
11: temperature measurement
12: stopcock The reactor 1 had a capacity of 1000 ml. The agitator speed was 500 rpm. The external circulation 3, reaction mixture circulation rate approximately 130 l/h, was operated by a pump. 735 g of aniline were introduced from the reservoir tank and mixed with 243 g of 30% strength aqueous hydrochloric acid. At a temperature of 40° C., a total of 204 g of a 50% strength solution of formaldehyde in water was then added within one hour at a constant metering rate to the circuit via the mixing element 6, a dynamic mixer. Directly after the addition of the formaldehyde solution, the reaction mixture was heated and then kept at 120° C. for 2.5 hours. The reaction mixture was worked up as described in comparative example 1. The N-methyl-MDA content in the resulting product was 0.07% by weight. This polyamine was reacted with phosgene in a two-stage process in the process according to the invention for preparing isocyanates. The hydrolyzable chlorine content in this polyisocyanate was 0.06%.

EXAMPLE 2

The procedure of Example 1 was followed, but the formaldehyde solution was added in a staged manner. In the first 30 minutes of the addition, the formaldehyde solution was metered into the reaction mixture at a rate of 306 g/h, and in the second 30 minutes at a rate of 102 g/h. The reaction mixture was worked up as described in Example 1. The N-methyl-MDA content in the resulting product was 0.08% by weight. This polyamine was reacted with phosgene in a two-stage process in a process for preparing isocyanates at a temperature of 80° C. and a pressure of 1 bar. The hydrolyzable chlorine content in this polyisocyanate was 0.07%. The iodine color index of the isocyanate was 15 at a dilution of 1:5 with monochlorobenzene.

The object of developing a process by which the undesired formation of N-methyl-MDA is prevented, could thus be achieved by the process according to the invention. Not only was the content of undesired N-methyl-MDA markedly decreased by 73 or 69%, but also the hydrolyzable chlorine content in the polyisocyanate which was produced using the MDA prepared according to the invention was drastically reduced by >70%. The object of preparing an isocyanate as light as possible starting from MDA was also achieved.

Both the MDA prepared according to the invention and the polyisocyanate produced using this MDA thus displayed substantially improved properties.

We claim:

1. A process for preparing polyisocyanates by phosgenation of methylenedianiline, prepared by reacting aniline with formaldehyde in the presence of acid catalysts, which comprises, in a semicontinuous process, introducing aniline with or without acid catalysts, feeding formaldehyde with or without acid catalyst through a mixing element into a circuit in which aniline with or without acid catalyst and with or without previously added formaldehyde is circulated and, after feeding in at least 50% of the total amount of formaldehyde to be fed in, heating the reaction mixture to a temperature above 75° C., wherein the phosgenation is carried out at temperatures of from 70 to 120° C. and at a pressure of from 0.8 to 5 bar via a two-step reaction in the presence of at least one inert organic solvent, the first phosgenation step being carried out in a static mixer and the second phosgenation step being carried out in a dwell-time apparatus wherein in the dwell-time apparatus the mass ratios of phosgene to hydrogen chloride being at the same time 10-30:1 in the liquid phase and 1-10:1 in the gas phase.

2. A process as claimed in claim 1, wherein the temperature in the first phosgenation step is from 90 to 120° C.

* * * * *